Figure 1:
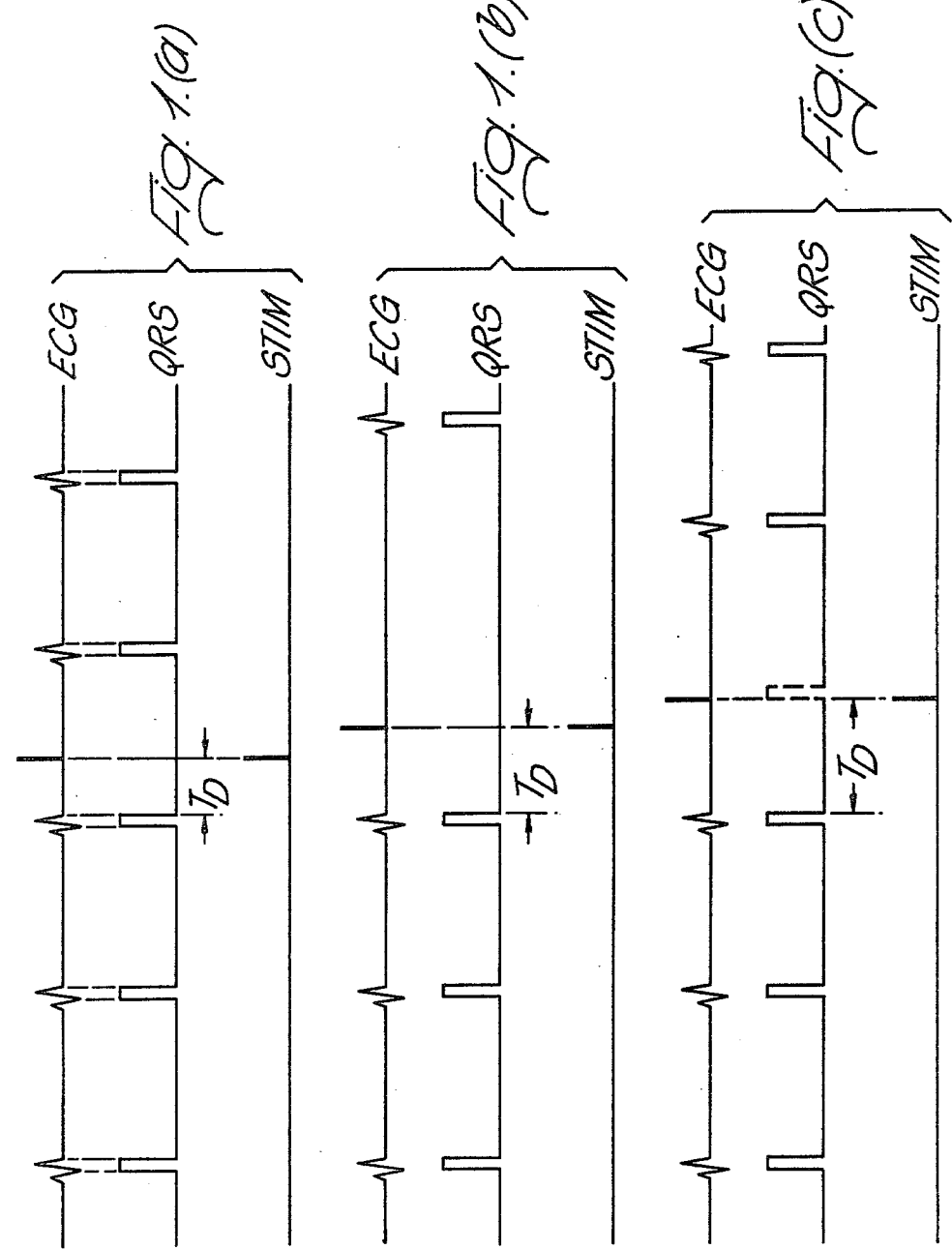

United States Patent [19]

Sowton et al.

[11] 4,312,356
[45] Jan. 26, 1982

[54] PACEMAKERS FOR TACHYCARDIA CONTROL

[75] Inventors: George E. Sowton, 10 Beach Ave., Sanderstead, Surrey, England; Alan J. Smale, London, England

[73] Assignee: George Edgar Sowton, Sanderstead, England

[21] Appl. No.: 124,667

[22] Filed: Feb. 26, 1980

[30] Foreign Application Priority Data

Mar. 7, 1979 [GB] United Kingdom ............... 07998/79

[51] Int. Cl.³ .............................................. A61N 1/36
[52] U.S. Cl. .............................................. 128/419 PG
[58] Field of Search ............................... 128/419 PG

[56] References Cited

U.S. PATENT DOCUMENTS 3,942,534 3/1974 Allen et al. .................... 128/419PG Primary Examiner—William E. Kamm
Attorney, Agent, or Firm—Steele, Gould & Fried

[57] ABSTRACT

A pacemaker for tachycardia control which comprises a detector for sensing the onset of a tachycardia, a generator responsive to the detector for issuing a stimulating pulse to the heart for arresting the tachycardia, a second detector for sensing the response of the heart to the stimulating pulse and if the tachycardia was not arrested, for determining if the pulse was issued at an incorrect early or late time relative to the tachycardia beat, and a controller for the stimulating pulse generator responsive to the second detector whereby, when the tachycardia is not arrested, to cause a subsequent stimulating pulse to be issued at an adjusted later or earlier time relative to the tachycardia beat.

17 Claims, 12 Drawing Figures

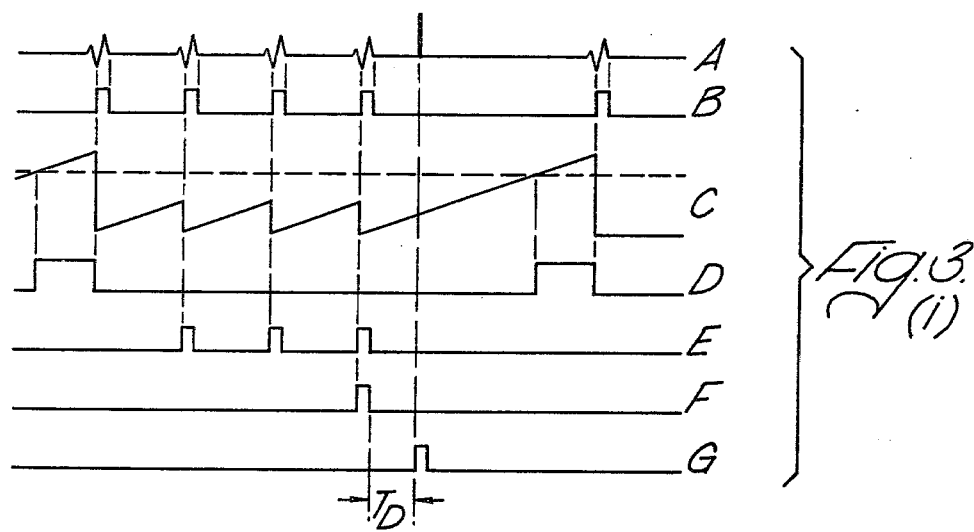
Fig. 3 (i)
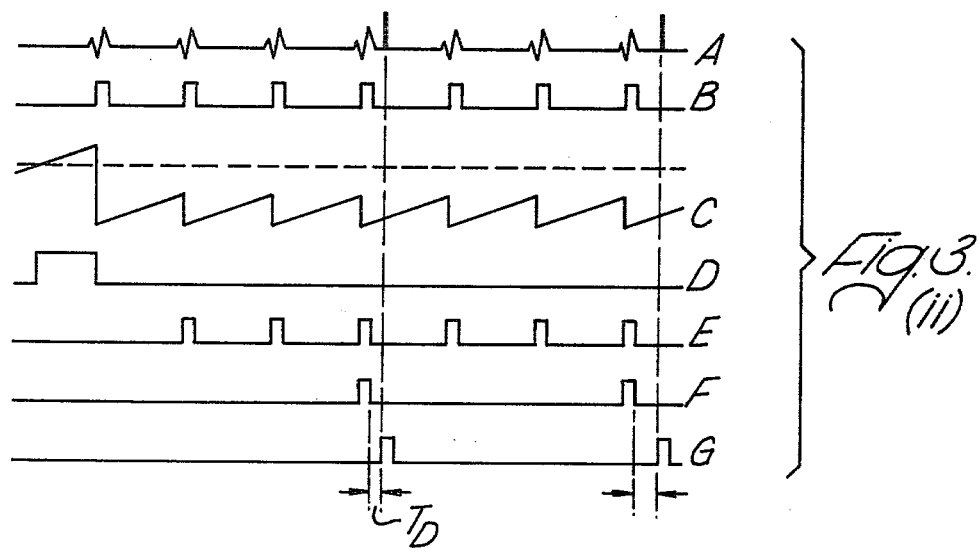
Fig. 3 (ii)

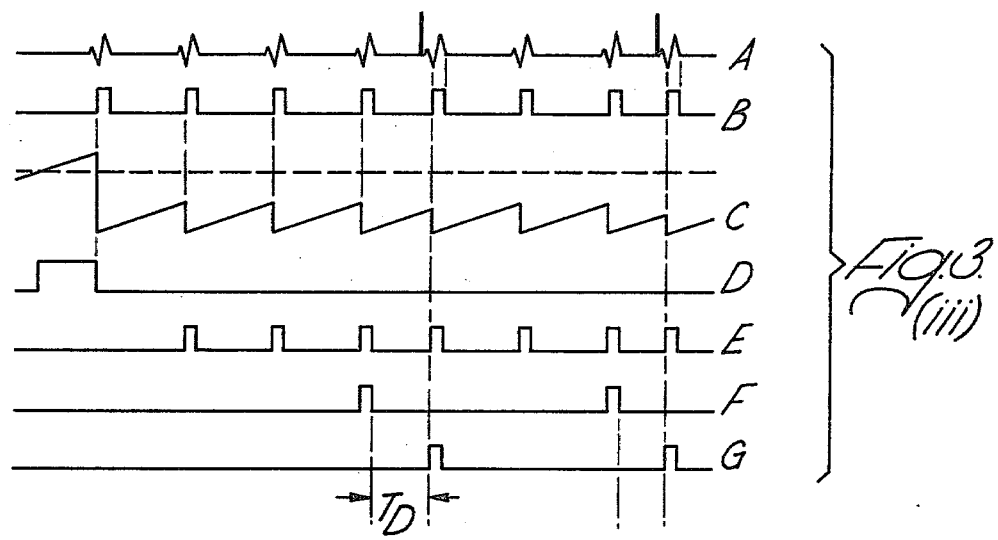
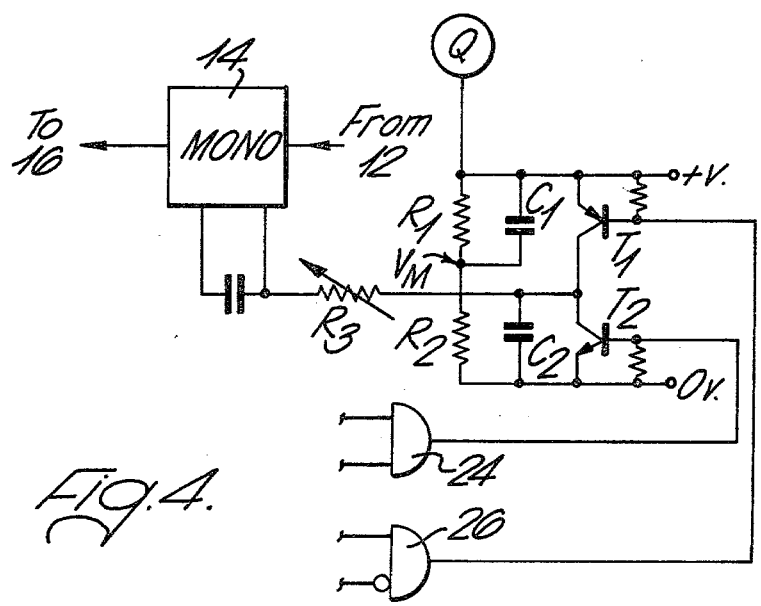

PACEMAKERS FOR TACHYCARDIA CONTROL

The most suitable principle for a pacemaker to terminate re-entry tachycardia requires the delivery of one or two critically timed stimuli during the tachycardia cycle. The period during the cycle at which the first stimulus must be delivered in order to terminate the tachycardia is referred to as the "window". At present, methods for providing stimulation during this window are:

1. The pacemaker is allowed to stimulate the heart at a different rate from the tachycardia so that sooner or later a random stimulus will fall during the window and terminate the tachycardia.

2. The entire cycle is scanned either from the beginning of the cycle outwards or from the end of the cycle inwards until the window is reached. The impulses are timed from the R wave of the tachycardia and changed by either (i) a fixed percentage of the cycle, or (ii) a fixed time interval until the window is detected and the tachycardia stops.

The present invention is concerned with a pacemaker which recognises the response to an ineffective stimulus and which adjusts the timing of subsequent stimuli accordingly.

According to the present invention, there is provided a pacemaker for tachycardia control which comprises means for detecting the onset of a tachycardia, means responsive to the detecting means for issuing one or more stimulating pulses to the heart for arresting the tachycardia, means for detecting the response of the heart consequential to the issuance of said stimulating pulse or pulses to determine whether said pulse or pulses were issued too early or too late in time relative to the tachycardia beats, and means for controlling the stimulating pulse issuing means in response to said last-mentioned detecting means whereby, in the case where said pulse or pulses were issued too early or too late, to increase or decrease, respectively, said time.

The manner in which a typical pacemaker according to the invention functions can be best understood from the following:

1. The pacemaker monitors the RR interval and will recognise the onset of the tachycardia in the usual way.

2. It delivers a premature stimulus, or two or more stimuli, with a delay from the R wave which is adjusted to be likely to fall into the window. This delay will be a preset proportion of the RR interval, commonly about one half.

3. If this stimulus causes no effect at all on the subsequent RR intervals this indicates that it has fallen too early, i.e. during the absolute refractory period of the heart. This will be detected because the pacemaker monitors subsequent RR intervals after delivering a stimulus. The number of beats monitored can be preset. The pacemaker will then deliver a further premature stimulus delayed from the timing of the first ineffective stimulus by either a fixed time or a fixed percentage. It will then again monitor the RR interval to determine if the tachycardia has stopped.

4. If the tachycardia has been terminated the pacemaker will revert to its inhibited mode in the usual way.

5. If the stimulus has again caused no change in the subsequent RR intervals then the procedure will be repeated so that the stimulus is further delayed, and the tachycardia again then monitored. This sequence of events will continue until the tachycardia stops; it is likely that only one ineffective stimulus will fall before the pacemaker corrects the timing to find the window.

6. If the initial stimulus falls too late, i.e. after the window, it will cause a premature beat but will not terminate the tachycardia. This premature beat will "reset" the tachycardia which will then continue at its previous rate. However, the resetting results in a shorter than usual interval to the next R wave and this can be detected by the pacemaker.

7. This will indicate the stimulus has been delivered too late and subsequent stimuli will be retimed either a fixed interval sooner or a fixed proportion sooner.

8. If this once again resets the tachycardia then the procedure will be repeated until the window is identified and the tachycardia terminated. It is very unlikely that more than one reset will be necessary for the pacemaker to correct the stimulus timing.

Figure 2:
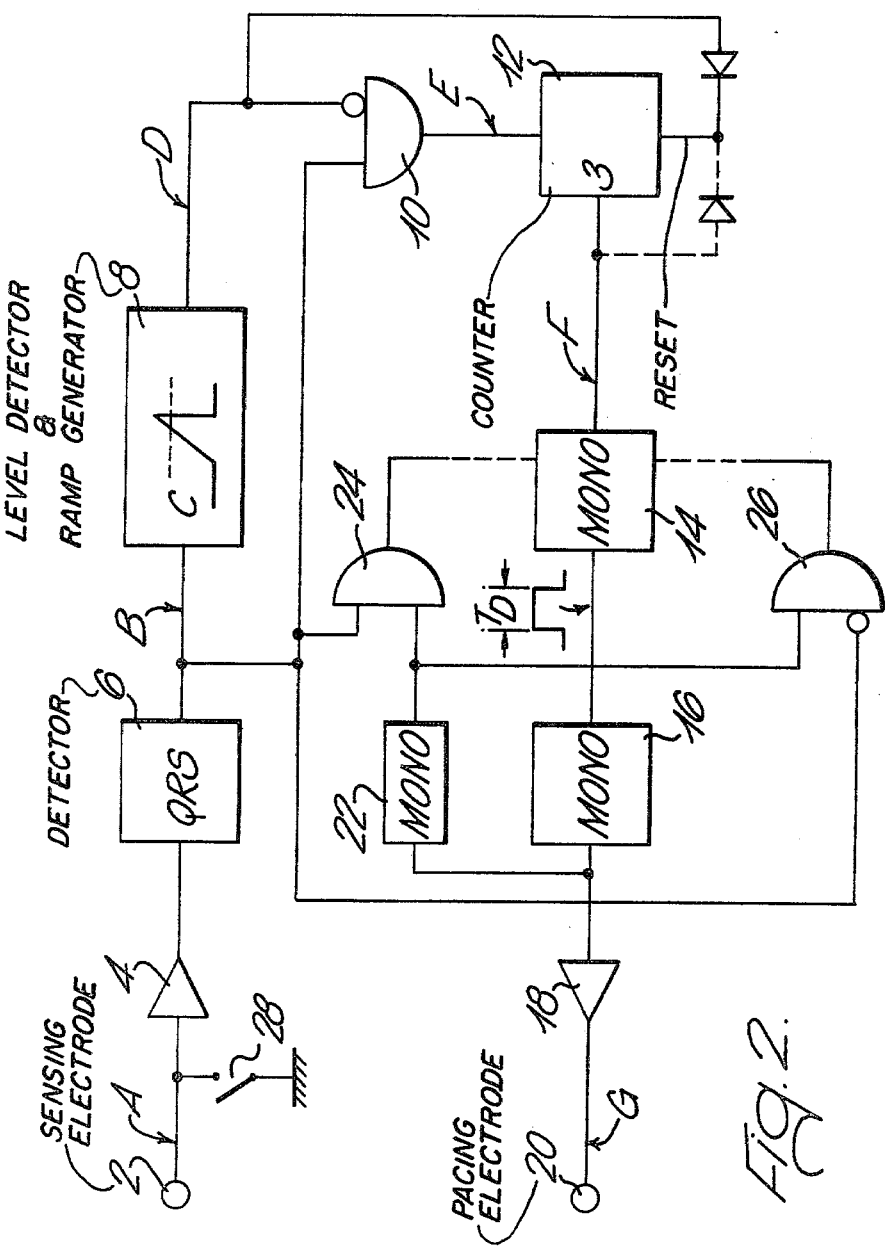
Figure 5:
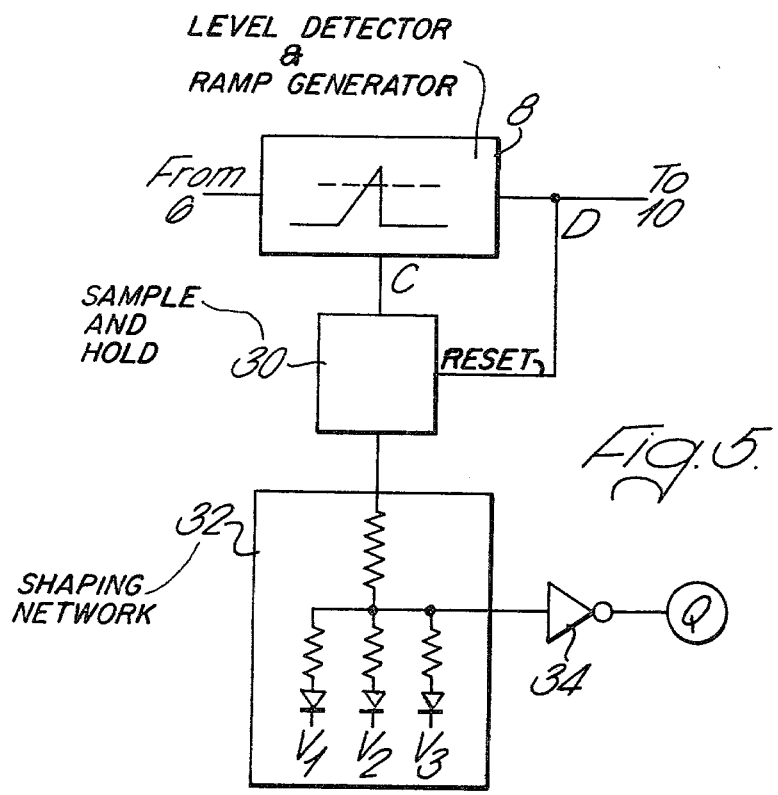
Figure 6:
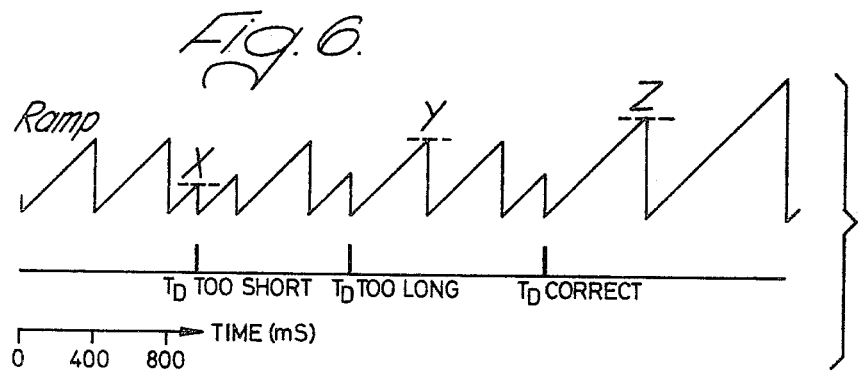
Figure 7:
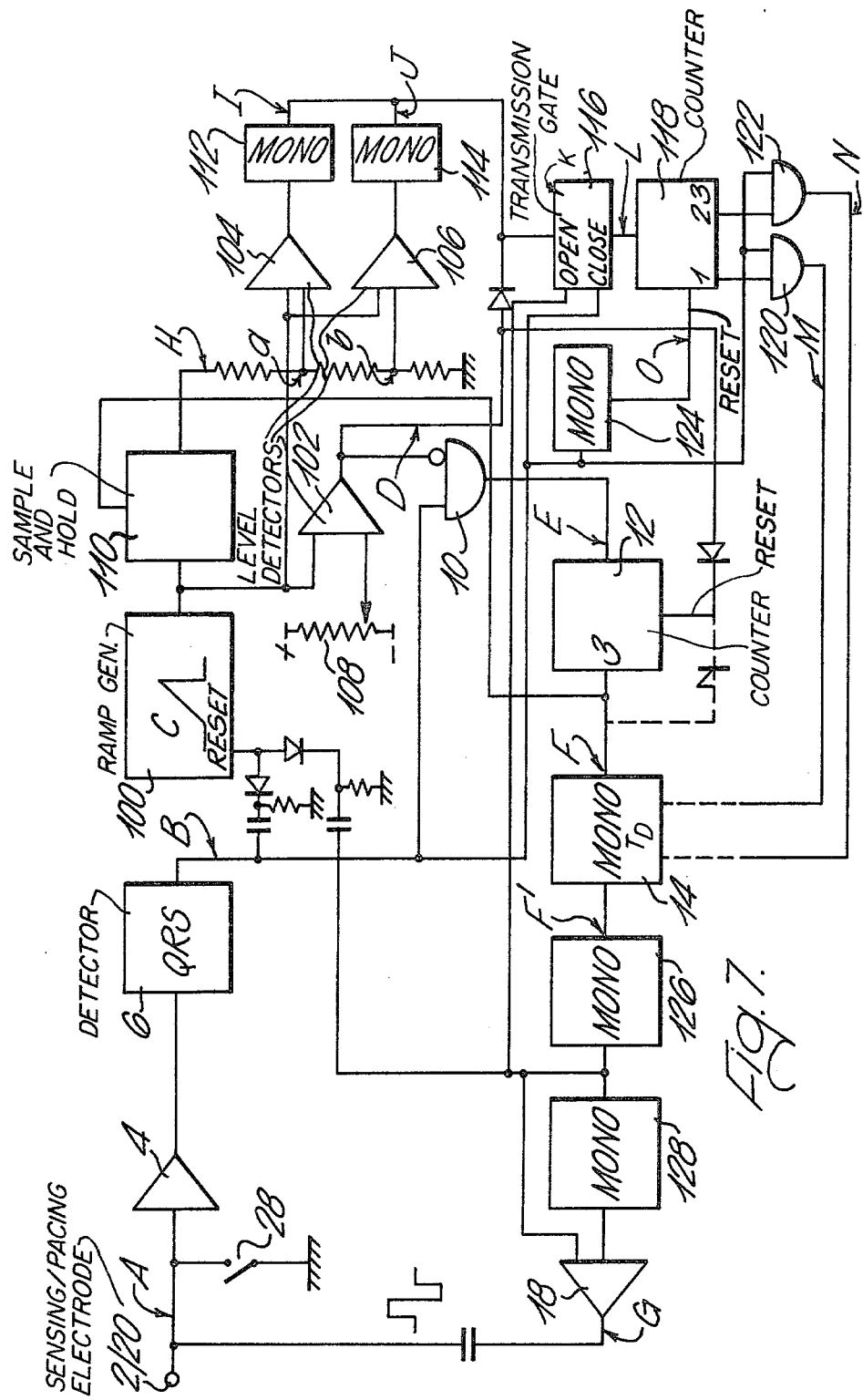
Figure 8:
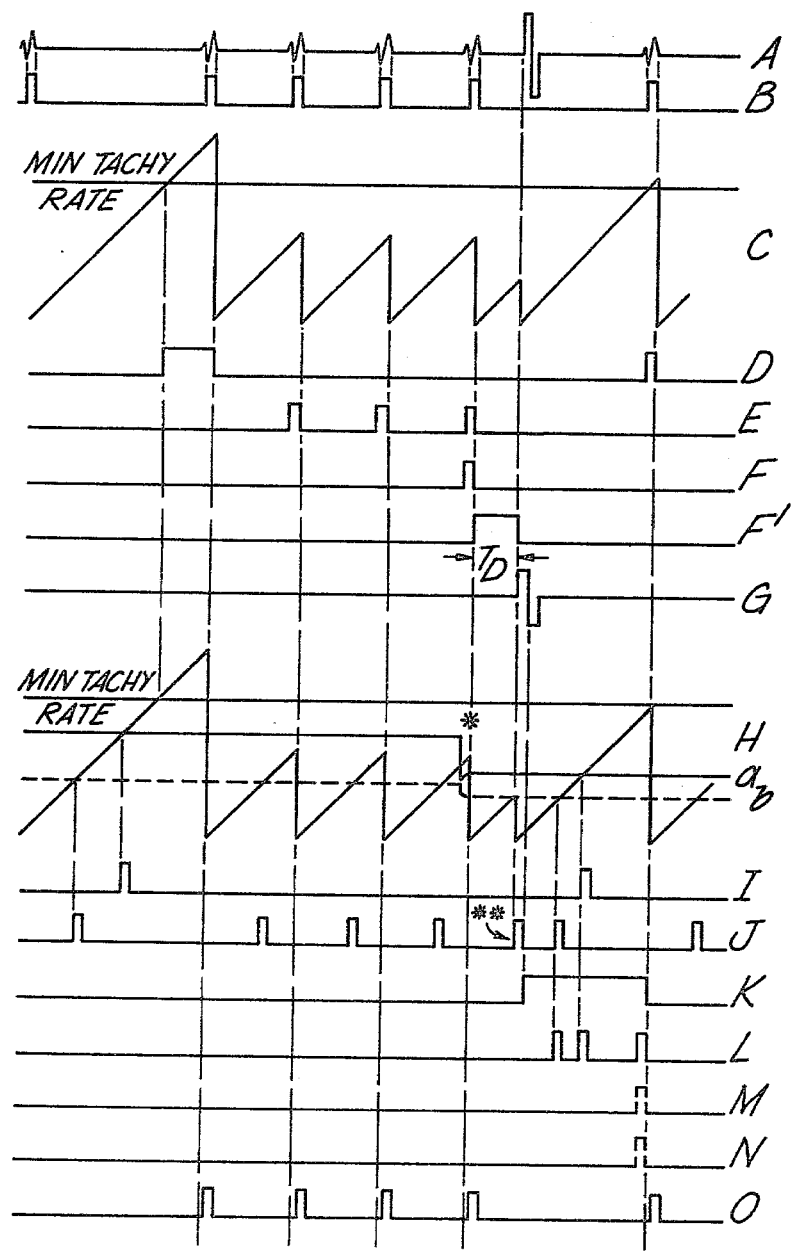

Preferred features of the invention will now be described with reference to the accompanying drawings, given by way of example, wherein:

FIGS. 1(a) to (c) are waveforms to assist in explaining the invention,

FIG. 2 is an electrical circuit diagram of a first embodiment of the invention,

FIGS. 3(i) to (iii) are waveforms at various points in the circuit of FIG. 2 and under various physiological circumstances, FIGS. 4 and 5 are electrical circuit diagrams of part of a pacemaker according to the invention, FIG. 6 are further waveforms, relating to a second embodiment of the invention, FIG. 7 is an electrical circuit diagram of the second embodiment of the invention, and FIG. 8 shows waveforms at various points in the circuit of FIG. 7.

The manner in which pacemakers according to the invention control tachycardia will first be described with reference to FIGS. 1(a) to (c). In each of FIGS. 1(a) to (c) three waveforms are shown—an ECG output ("ECG"), the output seen by a detector in the pacemaker responsive to QRS beats ("QRS"), and the stimulating pulses issued by the pacemaker in order to arrest tachycardia ("STIM").

FIG. 1(a) illustrates the situation where the stimulating pulse has been issued too early to arrest tachycardia (i.e. before the "window"). The pacemaker has detected the onset of tachycardia (for details see below) and has issued a stimulating pulse at a time $T_D$ from the last QRS beat. $T_D$ is too short, the stimulating pulse arises in the absolute refractory period of the heart and this has no effect on the tachycardia. $T_D$ needs to be increased to arrest tachycardia.

FIG. 1(b) illustrates the situation where the stimulating pulse has been issued at the correct time (i.e. within the "window"). $T_D$ is correct and the tachycardia is arrested.

FIG. 1(c) illustrates the situation where the stimulating pulse has been issued too late (i.e. after the "window"). This causes a paced beat but this will not terminate the tachycardia. This premature beat however resets the tachycardia which continues at its previous rate. The resetting results in an interval to the next R wave shorter than normal. In such a situation $T_D$ is too long and needs to be reduced to arrest tachycardia.

These different physiological conditions are detected by the pacemaker which subsequently alters $T_D$ (if necessary) to ensure termination of tachycardia:

(a) if $T_D$ is too early, the pacemaker detects that the stimulating pulse has had no effect on the tachycardia. It then increases $T_D$ to place the stimulating pulse within the window.

(b) if $T_D$ is correct and the tachycardia is arrested, the pacemaker issues no further stimulating pulses until a fresh tachycardia is detected.

(c) if $T_D$ is too late, the pacemaker detects this, for example either by detecting that the stimulating pulse caused a paced beat or by detecting that the R-R interval has been "reset". It then decreases $T_D$ to place the stimulating pulse within the window.

$T_D$ is progressively increased or decreased successively with each subsequent stimulating pulse issued, until the tachycardia is arrested. Initially $T_D$ is preset to a proportion of the RR interval during tachycardia and will commonly be about one half. Such a circumstance provides the most likely result that $T_D$ is correct upon the first occurrence of a stimulating pulse, but, if not, it is likely to be close to the window such that normally only one or two further stimulating pulses (at increased or decreased $T_D$ as the case may be) are issued.

A pacemaker for controlling tachycardia in the manner just described is illustrated in FIG. 2.

Referring to FIG. 2, a sensing electrode 2 supplies an input amplifier 4, the output of which is fed successively to a QRS detector 6, a ramp generator and level detector 8 and an AND gate 10 with one inverted input. The QRS detector 6 is typically a frequency selective network centred about the 17 ms half triangle, for example a twin T filter as in known pacemakers. The AND gate 10 controls a counter 12 supplying output pulses after a count of 3, these output pulses firing a monostable 14 of adjustable pulse width (see below). The monostable 14 controls a further monostable 16 (having an output pulse width of 0.5 ms). The output of monostable 16, after amplification by an output amplifier 18, is fed to a pacing electrode 20 whereby to provide a stimulus to the heart.

The output of monostable 16 is also fed to a further monostable 22 (10 ms pulse width) which in turn controls inputs on AND gates 24 and 26. The output from the QRS detector 6 is also supplied to inputs on AND gates 10, 24 and 26 (the latter input being inverted). The respective outputs from AND gates 24 and 26 control the pulse width of monostable 14 (see description below in relation to FIG. 4). The counter 12 is reset by its own output or by the output from the ramp generator and level detector 8.

The input from sensing electrode 2 is muted during a pacing stimulus to reduce the likelihood of the stimulus causing the input amplifier 4 to block. Although this muting is shown schematically as a switch 28, in practice it would be accomplished electronically, such as in the input amplifier 4 before the first AC coupling.

The operation of the pacemaker will be described with reference to FIGS. 3(i) to (iii), where the waveforms shown (schematically) are at positions A to G in FIG. 2.

Every output from QRS detector 6 (waveform B) resets the ramp generator 8. If the ramp (waveform C) rises to above a preset level (which is set dependent upon the minimum tachycardia rate at which the pacemaker is to operate) a pulse (waveform D) is generated which finishes slightly after the trailing edge of the QRS pulse. The AND gate 10 only provides output pulses when input pulses are received from the QRS detector 6 and when input pulses from the level detector in 8 are absent. This condition arises only when the heart is in a tachycardia situation.

Every 3 output pulses from AND gate 10 (waveform E) provide an output from counter 12 (waveform F). The latter output fires the monostable 14 of adjustable pulse width (shown as $T_D$) which in turn causes a stimulus pulse to be issued by pacing electrode 20 (waveform G).

The adjustable pulse width of monostable 14 ($T_D$) is employed to ensure that the stimulating pulses are issued within the window necessary to terminate the tachycardia.

If the first stimulating pulse to be issued is correctly timed (see FIG. 1(b)) then the pulse width $T_D$ is correct and the tachycardia ceases. This situation is illustrated in FIG. 3(i).

If the first stimulating pulse to be issued is too early (see FIG. 1(a)) then $T_D$ is too short and the pulse has fallen within the absolute refractory period of the heart and does not cause a QRS pulse. The production of a stimulus pulse without a corresponding QRS pulse is detected by AND gate 26 which issues a pulse to increase $T_D$ of monostable 14 (see below). The next three tachycardia pulses will cause a further firing of monostable 14 but at increased $T_D$. A cycle of stimulating pulses are thus issued at successively increased $T_D$ until the tachycardia is arrested or $T_D$ becomes too long and a paced beat results. This situation, $T_D$ too short, is illustrated in FIG. 3(ii).

If the first stimulating pulse to be issued is too late (see FIG. 1(c)) then $T_D$ is too long. The stimulus thus causes a paced beat. The coincidence of a paced beat following a stimulating pulse is detected by AND gate 24 which issues a pulse to decrease $T_D$ of monostable 14 (see below). A reversal of the operation described in the preceding paragraph arises: $T_D$ will be progressively reduced until the window is reached and the tachycardia is arrested or $T_D$ becomes too short and the paced beats cease. This situation is illustrated in FIG. 3(iii).

A typical circuit for controlling $T_D$ is illustrated in FIG. 4. Initially $V_M$ is quickly established by $C_1$ and $C_2$; the ratios $R_1:R_2$ and $C_1:C_2$ being the same. $V_M$ may be raised or lowered by switching on $T_1$ and $T_2$ for discrete periods and this will shorten or lengthen $T_D$ accordingly. The resistor $R_3$ is preset to an average $T_D$ for the particular patient under treatment. This $T_D$ is a specific preset proportion of the RR interval of the patient at any particular time. If it is desired to cause this proportion to vary with a variation in the RR interval, this can be achieved, for example, by coupling the circuit shown in FIG. 5, at point Q, to the circuit shown in FIG. 4. A sample and hold circuit 30 holds the peak value of the ramp voltage generated in 8 and is reset by the output of the level detector in 8. The output of circuit 30 is passed through a shaping network 32 and invertor 34 to point Q in FIG. 4.

The above described embodiment employs separate sensing and pacing electrodes to minimise blocking problems on the input amplifier 4. When a stimulus is delivered, the capacitive effect or surface layer effect causes the sensing electrode to become polarised and the waveform consequently has a long, decaying tail. This long tail may cause the amplifier to block even despite the muting provided. This may be unacceptable with rapid tachycardias since, if the stimulus pulse is too early ($T_D$ too short), then the input amplifier must be unblocked and functioning normally very soon thereafter to detect the next tachycardia beat. Other than using separate electrodes, a bipolar electrode may be employed or a biphasic stimulating pulse. The latter pulse (going rapidly both positive and negative) will charge and discharge the surface layer equally and the net effect will leave little or no charge and no long tail to block the amplifier.

An alternative embodiment of the invention will now be described. Assume that the ramp voltage produced in circuit 8 above (i.e. waveform C, FIGS. 3(i)-(iii)) is reset by the output of the QRS detector 6, or by the stimulus pulses issued to the heart, except when a paced beat is produced by a too late stimulus. FIG. 6 shows the ramp waveforms for a tachycardia of 150 ppm, together with stimulus pulses issued too early, too late, and correctly in time. In such circumstances the ramp peaks after a too early, a too late, or a correct stimulus (peaks X, Y, and Z, respectively) are always in an ascending order and a good ratio can be maintained between them. If the ramp after a stimulus reset is passed through three level detectors (one sensitive just to peak X, one sensitive just to peak Y and one sensitive to Z) then one pulse will be produced if the stimulus is too early, two pulses will be produced if the stimulus is too late and three pulses will be produced if the stimulus is correct.

A pacemaker circuit for accomplishing tachycardia control in this manner is shown in FIG. 7, where components common to those in FIG. 2 are given identical reference numerals. A single sensing/pacing electrode 2/20 with biphasic stimulus pulses is employed. A ramp generator 100 is reset by the trailing edge of pulses from the QRS detector 6 and feeds level detectors 102, 104, 106. The level at which detector 102 is actuated is controlled by variable resistor 108 which acts to set the minimum tachycardia rate at which the pacemaker is to operate. The ramp generator 100 also feeds a sample and hold circuit 110, the output of which is fed to the level setting inputs of detectors 104 and 106 (at a and b respectively). The outputs of the level detectors 104 and 106, after passage through monostables 112, 114, and transmission gate 116 actuates a counter 118. The output of level detector 102 is also supplied to gate 116. The counter 118 counts up to three and the "1" and "2" outputs are supplied to AND gates 120 and 122 respectively. Second inputs to AND gates 120 and 122 are provided from the QRS detector 6. The outputs of AND gates 120 and 122 are employed to control the pulse width $T_D$ of monostable 14 in the manner accomplished by AND gates 24 and 26 in FIGS. 2 and 4. The QRS detector output is also employed to close transmission gate 116 and, after passage through a delay monostable 124, to reset counter 118.

The counter 12 supplies the sample signal to sample and hold circuit 110. The monostable 14 feeds a pair of monostables 126, 128 each of 0.5 ms pulse width. Outputs from both 126, 128 are provided to output amplifier 18 whereas the output of monostable 126 is also employed to reset the ramp generator 100 and open transmission gate 116.

The operation of the circuit shown in FIG. 7 will be described with reference to FIG. 8, which illustrates waveforms at various points in the circuit when the pulse width $T_D$ is correctly selected for the first stimulus pulse issued. Waveforms A to G have already been described with reference to the previous embodiment (see FIGS. 3(i) to (iii)). Waveform $F^1$ shows additionally the output of monostable 14 providing the adjustable pulse width $T_D$. Referring to the reference voltages a and b fed to level detectors 104 and 106, these are selected to detect peaks X and Z previously described, b being approximately a/2.

The detection circuitry does not come into operation until a third tachycardia pulse is observed. At this point (* in waveform H) the sample and hold circuit 110 passes a voltage to level detectors 104 and 106. A pulse is produced by monostable 114 as the ramp passes voltage b (waveform J). A pulse is produced by monostable 112 as the ramp passes voltage a (waveform I).

The pulse marked ** in J may or may not be present but it is of no consequence. The transmission gate 116, opened by the issuance of the stimulus pulse, passes these two pulses, together with that produced from level detector 102 (waveform D) to counter 118 (waveform L). The output of gate 116 is the gated sum of waveforms D, I, and J (in this case 3). Since we have assumed that, in this case, $T_D$ is correct and the tachycardia has been arrested, the pacemaker takes no further action (until a fresh tachycardia is detected). In such a circumstance no output is supplied to the delay monostable 14 via AND gates 120 and 122 (i.e. $T_D$ is not adjusted).

However, now assume that $T_D$ is too short. As explained with reference to FIG. 6 this results in a ramp peak "X" which is much smaller than the corresponding peak "Z" for a correctly timed $T_D$. This results in outputs not being supplied by level detectors 104 and 106 since the ramp does not achieve voltages a or b during the sample and hold period. The first and second pulses in waveform L would be absent and counter 118 would count only to 1. This would enable AND gate 120 to provide an output pulse (waveform M—the pulse shown in phantom in FIG. 8) which would be employed to increase $T_D$ as previously described.

Alternatively, if $T_D$ is too long, then as explained with reference to FIG. 6, this results in a ramp peak "Y" greater than ramp peak "X" ($T_D$ too short) but not as great as the ramp "Z" ($T_D$ correct). This results in an output being supplied by level detector 106 ("Y" being greater than voltage b) but not by level detector 104 ("Y" being less than voltage a). This results in a count of 2 being held by counter 118 and an output provided by AND gate 122 (waveform N—the pulse shown in phantom in FIG. 8). This is employed to decrease $T_D$ as previously described.

Although the counter 12 in FIG. 7 is shown as being reset by level detector 102, in an alternative embodiment it can be reset by its own output. In such an alternative embodiment (not illustrated), the reset connection from level detector 102 to counter 12 would be disconnected and replaced with a line, the line including a diode, connecting the output "3" of counter 12 to the reset input thereof. It is preferred to employ the output of counter 12 to reset itself when attempting to detect tachycardia conditions not far removed from normal cardiac beat conditions (in terms of beat interval). If the level detector 102 is used to reset counter 12 under such conditions, difficulties can arise in the circuit. On the other hand, resetting counter 12 from the level detector 102 rather than from its own output results in a faster response for the pacemaker (this applies also to the FIG. 2 embodiment).

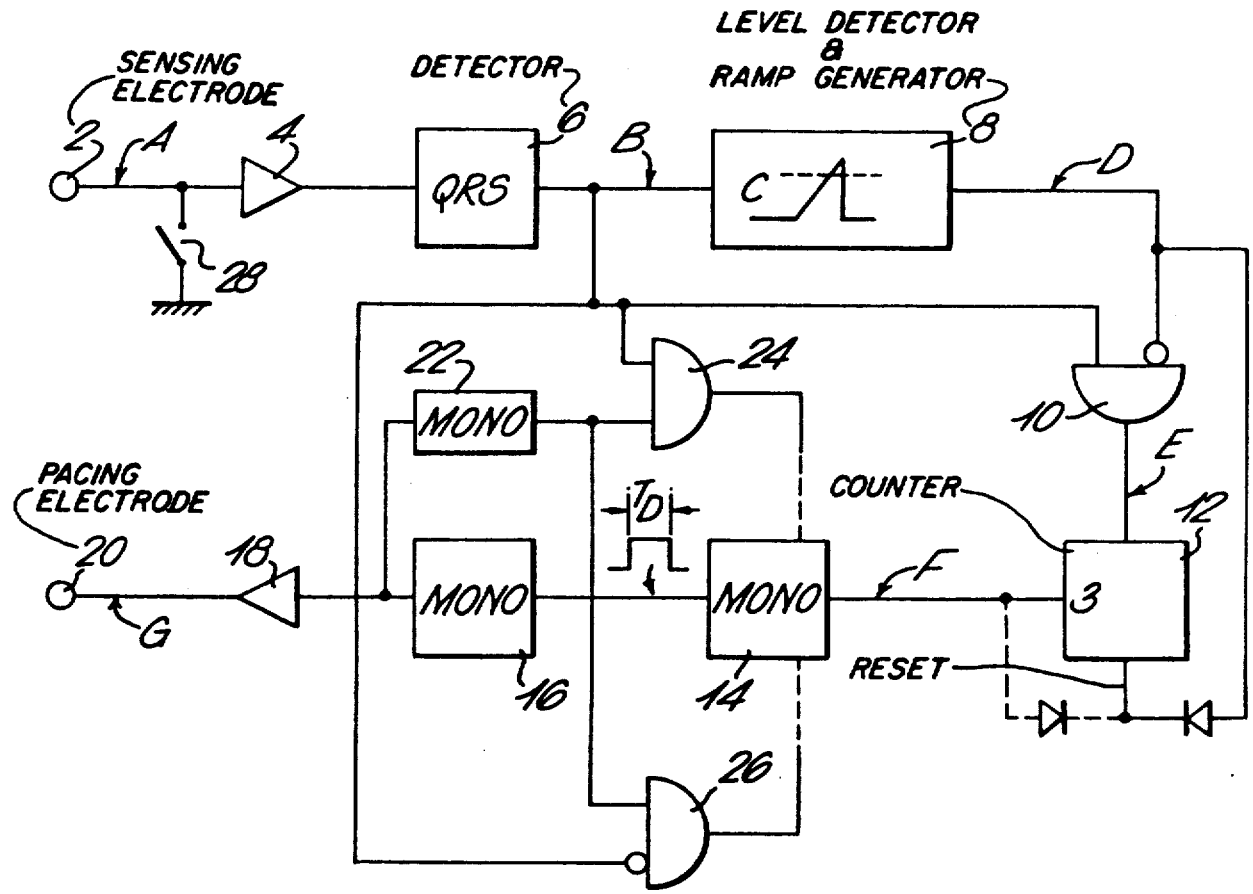

I claim:
1. A pacemaker for tachycardia control, comprising: means for sensing the onset of a tachycardia;

means responsive to said sensing means for issuing a stimulating pulse to the heart for arresting the tachycardia;

means for detecting the response of the heart to said stimulating pulse and, if said tachycardia was not arrested, for determining which of an incorrect early or late time said pulse was issued relative to the tachycardia beat; and, means for controlling the stimulating pulse issuing means in response to said detecting means whereby, when the tachycardia is not arrested, to cause a subsequent stimulating pulse to be issued at an adjusted later or earlier time relative to the tachycardia beat, the subsequent pulse being issued later if the previous pulse was too early and being issued earlier if the previous pulse was too late.

2. A pacemaker according to claim 1, wherein the controlling means is repetitively operable to cause the stimulating pulse issue time to be adjusted in steps until a pulse is issued at the correct time to arrest the tachycardia.

3. A pacemaker according to claims 1 or 2, wherein the stimulating pulse issuing means includes a fixed pulse width monostable output circuit; and, the controlling means includes a variable pulse width monostable for triggering the fixed pulse width monostable and circuit means responsive to the heart response detecting means for adjusting the width of pulses supplied by the variable pulse width monostable.

4. A pacemaker according to claim 3, wherein the fixed pulse width monostable output circuit is triggered by the trailing edge of a pulse supplied by the variable pulse width monostable and the circuit means is responsive to the detecting means to advance or retard the trailing edge switching of the variable pulse width monostable.

5. A pacemaker according to claim 4, wherein said circuit means comprises a biassing circuit which can be set for a nominal pulse width, and means for supplying current pulses to said biassing circuit to adjust the biassing level thereof up or down in order to increase or decrease said pulse width from its nominal value.

6. A pacemaker according to claim 5, wherein said biassing circuit can be adjustably set for a nominal pulse width most likely to cause issue of a stimulating pulse at the correct time.

7. A pacemaker according to claim 5, further comprising a monitoring circuit which monitors the heart beat rhythm and adjusts the biassing level of the biassing circuit in order to vary the nominal pulse width in accordance with variations in said rhythm.

8. A pacemaker according to claim 1, wherein said sensing means comprises a sensing electrode, a beat detector passing pulses responsive to the sensed heart beats, a ramp generator fed with the detector pulses, a voltage level detector connected to the ramp generator and a gate circuit fed with the detector pulses and pulses from the ramp generator produced when the voltage level rises above a predetermined value, said gate circuit being selectively responsive to its two inputs to supply output pulses to a stimulating pulse initiator when a tachycardia is sensed.

9. A pacemaker according to claim 8, wherein said gate circuit is an AND gate having an inverted input and provides output pulses only when detector pulses are present and ramp generator produced pulses are absent.

10. A pacemaker according to claims 8 or 9, wherein the stimulating pulse initiator comprises a counter adapted to issue a stimulating pulse responsive to supply of a predetermined plurality of output pulses received from the gate circuit.

11. A pacemaker according to claim 8, wherein the stimulating pulse issuing means includes a fixed pulse width monostable output circuit; and, the controlling means including a variable pulse width monostable for triggering the fixed pulse width monostable and circuit means responsive to the heart response detecting means for adjusting the width of pulses supplied by the variable pulse width monostable, and the output of the stimulating pulse initiator is used to trigger the variable pulse width monostable of the controlling means.

12. A pacemaker according to claim 11, wherein the detecting means comprises two gate circuits supplied at a first input with the fixed width stimulating pulses of the fixed pulse width monostable and at a second output with the heart beat responsive pulses from the beat detector, the output of one gate circuit causing an increase in the width of pulses supplied by the variable pulse width generator when a stimulating pulse is issued at an incorrect early time and the output of the other gate circuit causing a decrease in the width of pulses supplied by the variable pulse width generator when a stimulating pulse is issued at an incorrect late time.

13. A pacemaker according to claim 11, wherein the voltage level detector comprises two supplementary voltage level detectors connected to the ramp generator, which is reset responsive to generation of the stimulating pulses, a feedback circuit whereby the supplementary voltage level detectors are respectively operative at differing voltage levels representative of two of the three conditions given by a correctly timed stimulating pulse, an incorrectly timed early stimulating pulse and an incorrectly timed late stimulating pulse, and a counter receiving the output pulses of the first mentioned voltage level detector and the two supplementary voltage level detectors and being selectively responsive to the number of output pulses received to provide an output to the first input of either one of two gate circuits only when the stimulating pulse is incorrectly timed, the gate circuits being provided at a second input with the heart beat responsive pulses from the beat detector, the output of one gate circuit causing an increase in the width of pulses supplied by the variable pulse width generator when a stimulating pulse is issued at an incorrect early time and the output of the other gate circuit causing a decrease in the width of pulses supplied by the variable pulse width generator when a stimulating pulse is issued at an incorrect late time.

14. A pacemaker according to claim 13, wherein the feedback circuit includes a sample and hold circuit fed with the output of the ramp generator and with the output pulses of the stimulating pulse initiator.

15. A pacemaker according to claim 1, having separate sensing and pacing electrodes.

16. A pacemaker according to claim 1, having a common sensing and pacing electrode supplied with biphasic stimulating pulses.

17. A pacemaker according to claim 16, wherein the stimulating pulse issuing means includes a fixed pulse width monostable output circuit comprising two monostables providing respective outputs to an output amplifier; and, the controlling means includes a variable pulse width monostable for triggering the fixed pulse width monostable and circuit means responsive to the heart response detecting means for adjusting the width of pulses supplied by the variable pulse width monostable.

* * * * *

UNITED STATES PATENT AND TRADEMARK OFFICE
CERTIFICATE OF CORRECTION

PATENT NO. : 4,312,356

DATED : January 26, 1982

INVENTOR(S) : George E. Sowton, et al

It is certified that error appears in the above-identified patent and that said Letters Patent is hereby corrected as shown below:

The title page should be deleted to appear as per attached title page.

Signed and Sealed this

Thirtieth Day of November 1982

[SEAL]

Attest:

GERALD J. MOSSINGHOFF

Attesting Officer

Commissioner of Patents and Trademarks

United States Patent [19]

Sowton et al.

[11] 4,312,356
[45] Jan. 26, 1982

[54] PACEMAKERS FOR TACHYCARDIA CONTROL

[75] Inventors: George E. Sowton, 10 Beach Ave., Sanderstead, Surrey, England; Alan J. Smale, London, England

[73] Assignee: George Edgar Sowton, Sanderstead, England

[21] Appl. No.: 124,667

[22] Filed: Feb. 26, 1980

[30] Foreign Application Priority Data

Mar. 7, 1979 [GB] United Kingdom ............... 07998/79

[51] Int. Cl.³ .............................................. A61N 1/36
[52] U.S. Cl. .............................................. 128/419 PG
[58] Field of Search .................................. 128/419 PG

[56] References Cited

U.S. PATENT DOCUMENTS 3,942,534 3/1974 Allen et al. .................. 128/419PG Primary Examiner—William E. Kamm
Attorney, Agent, or Firm—Steele, Gould & Fried

[57] ABSTRACT

A pacemaker for tachycardia control which comprises a detector for sensing the onset of a tachycardia, a generator responsive to the detector for issuing a stimulating pulse to the heart for arresting the tachycardia, a second detector for sensing the response of the heart to the stimulating pulse and if the tachycardia was not arrested, for determining if the pulse was issued at an incorrect early or late time relative to the tachycardia beat, and a controller for the stimulating pulse generator responsive to the second detector whereby, when the tachycardia is not arrested, to cause a subsequent stimulating pulse to be issued at an adjusted later or earlier time relative to the tachycardia beat.

17 Claims, 12 Drawing Figures